United States Patent
White

(10) Patent No.: US 11,268,101 B2
(45) Date of Patent: Mar. 8, 2022

(54) RECOMBINANT PROTEIN PRODUCTION

(71) Applicant: The University of York, York (GB)

(72) Inventor: Robert White, York (GB)

(73) Assignee: The University of York, York (GB)

( * ) Notice: Subject to any disclaimer, the term of this patent is extended or adjusted under 35 U.S.C. 154(b) by 650 days.

(21) Appl. No.: 16/065,421

(22) PCT Filed: Jan. 9, 2017

(86) PCT No.: PCT/GB2017/050028
§ 371 (c)(1),
(2) Date: Jun. 22, 2018

(87) PCT Pub. No.: WO2017/121988
PCT Pub. Date: Jul. 20, 2017

(65) Prior Publication Data
US 2018/0362992 A1   Dec. 20, 2018

(30) Foreign Application Priority Data

Jan. 12, 2016   (GB) ..................................... 1600512

(51) Int. Cl.
| | |
|---|---|
| *C12N 15/11* | (2006.01) |
| *C12N 15/67* | (2006.01) |
| *C12N 15/81* | (2006.01) |
| *C12P 21/02* | (2006.01) |
| *C12N 15/62* | (2006.01) |

(52) U.S. Cl.
CPC ............. *C12N 15/81* (2013.01); *C12N 15/67* (2013.01); *C12P 21/02* (2013.01); *C12N 15/11* (2013.01); *C12N 15/62* (2013.01)

(58) Field of Classification Search
CPC .......... C12N 1/36; C12N 15/67; C12N 15/11; C12N 15/62; C12N 15/81; C12P 21/02
USPC .......... 435/69.1, 6.12, 320.1; 536/23.1, 24.33
See application file for complete search history.

(56) References Cited

U.S. PATENT DOCUMENTS

| 2005/0028639 A1 | 12/2005 | Kwon et al. |
| 2013/0149699 A1 | 6/2013 | Barral et al. |

FOREIGN PATENT DOCUMENTS

| EP | 1 911 840 A1 | 4/2008 |
| EP | 2 246 428 A1 | 11/2010 |
| JP | 2016-154502 A | 9/2016 |
| WO | WO 2000/012728 A1 | 3/2000 |
| WO | WO 2000/044926 A1 | 8/2000 |
| WO | WO 2004/024915 A1 | 3/2004 |
| WO | WO 2004/085463 A2 | 10/2004 |
| WO | WO 2007/103307 A2 | 9/2007 |
| WO | WO 2008/073184 A2 | 6/2008 |
| WO | WO 2009/058812 A1 | 5/2009 |
| WO | WO 2014/140347 A2 | 9/2014 |
| WO | WO 2014/160032 A1 | 10/2014 |
| WO | WO 2015/048989 A1 | 4/2015 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Agris et al., "tRNA's Wobble Decoding of the Genome: 40 Years of Modification," *J Mol Biol*. 366:1-13, 2007.
Iben and Maraia, "tRNAomics: tRNA gene copy number variation and codon use provide bioinformatic evidence of a new anticodon:codon wobble pair in a eukaryote," *RNA* 18:1358-1372, 2012.
Johansson et al., "Genetic Code Translation Displays a Linear Trade-Off Between Efficiency and Accuracy of tRNA Selection," *Proc Natl Acad Sci U.S.A.* 109:131-136, 2012.
Seligmann, "Error compensation of tRNA misacylation by codon-anticodon mismatch prevents translational amino acid misinsertion," *Comput Biol Chem*. 35:81-95, 2011.
Wald et al., "Codon usage bias in prokaryotic pyrimidine-ending codons is associated with the degeneracy of the encoded amino acids," *Nucleic Acids Res*. 40:7074-7083, 2012.
GB1600512.6 Search Report dated Oct. 14, 2016 (4 pages).
PCTGB2017050028 International Search Report and Written Opinion dated Apr. 5, 2017 (15 pages).
Behura & Severson, "Coadaptation of Isoacceptor tRNA genes and codon usage bias for translation efficiency in *Aedes aegypti* and *Anopheles gambiae*," *Insect Mol Biol*. 20:177-187, 2011.
Brown, T.A., Genomes—An Approach to New Bioinformation Systems [in Japanese], Medical Science International, 1st edition, May 26, 2000, pp. 262, 263, 463.
English translation of Office Action dated Aug. 17, 2021 in Japanese Patent Application No. 2018-534839 (8 pages).

* cited by examiner

*Primary Examiner* — Robert B Mondesi
*Assistant Examiner* — Mohammad Y Meah
(74) *Attorney, Agent, or Firm* — Klarquist Sparkman, LLP

(57) ABSTRACT

The disclosure relates to recombinant protein expression systems comprising genetically modified cells wherein the cells are transformed or transfected with tRNA genes to reduce base mismatch due to genetic degeneracy in the genetic code.

15 Claims, 11 Drawing Sheets
Specification includes a Sequence Listing.

Figure 8

| Site of Error | Error Rate -YIN | Error Rate +YIN | Error Suppression |
|---|---|---|---|
| L chain N156 | 0.0466% | 0.00147% | 32-fold |
| H chain N307 | 0.0102% | 0.00114% | 9-fold |
| H chain N336 | 0.277% | 0.0263% | 11-fold |
| H chain N405 | 0.147% | 0.037% | 4-fold |

SEQUENCE LISTING

<160> NUMBER OF SEQ ID NOS: 10

<210> SEQ ID NO 1
<211> LENGTH: 583
<212> TYPE: DNA
<213> ORGANISM: Homo sapiens

<400> SEQUENCE: 1

| | | | | | | |
|---|---|---|---|---|---|---|
| ttagatctgc | ggccgcgtga | gcagggtgca | cttgctgctt | ttgtgccgct | ttaatgagtt | 60 |
| cacacagcag | aatacctaaa | tctgcacaga | accttggtta | acattttaag | gtaggcaaac | 120 |
| gcaggcatac | caacttgttc | ctgttgccat | tgcagtgact | aaaggaggga | tgtcacaggg | 180 |
| tattaattac | agagcaggcc | atatgctatt | tttgtacagt | aatcctttcc | ttttttccc | 240 |
| cattttctt | aaatcttaaa | aataagactg | aattctgata | tcaagagtta | aggtcccttc | 300 |
| aatagttcag | ctggtagagc | agaggactat | agctacttcc | tcagtaggag | acgtccttag | 360 |
| gttgctggtt | cgattccagc | ttgaaggaga | caagtacagt | tttggctggg | cacggtggtt | 420 |
| catggctgta | atcacagcac | tttgggaggt | taaggcaggt | ggatcacgag | gtcaggagat | 480 |
| caagatcatc | ctggccaatg | tggtgaaact | ctgtctccgg | tgcgggtgcc | agggcgtgcc | 540 |
| cttgggctcc | ccgggcgcgt | actccacgcg | gccgcctcga | gtt | | 583 |

<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
gctggtagag cagaggacta t                                              21

<210> SEQ ID NO 3
<211> LENGTH: 21
<212> TYPE: DNA
<213> ORGANISM: artificial sequence
<220> FEATURE:
<223> OTHER INFORMATION: primer

<400> SEQUENCE: 3
tcgaaccagc aacctaagga c                                              21

<210> SEQ ID NO 4
<211> LENGTH: 1003
<212> TYPE: DNA
<213> ORGANISM: Homo sapiens

<400> SEQUENCE: 4

| | | | | | | |
|---|---|---|---|---|---|---|
| agatcttcta | gagtttaaac | cgccgctcac | agtacccgaa | aggcgcattt | ttcacaaact | 60 |
| gttgtagaaa | gagttcatgg | cggggtggcg | gcgggaaaaa | aaaaaaaaa | gctaacgccg | 120 |
| tggccggtgc | gggagtcgag | cccgcgacct | tggtgttatc | agcaccacgc | tcttaccaac | 180 |
| tgagctaacc | ggccgcctga | cggcacagtg | cccctgagc | gtataaaagg | gctccacgtt | 240 |
| cgcgcccgtc | cacgagcgat | tcctcgccaa | gccgcgcgc | ctctggctgc | cttccgcttt | 300 |
| gccccagccg | cggggactcc | ggggaggagc | caccgcccca | gcgctggccg | ggtttctccc | 360 |
| gctcctcct | gccaggctgt | cctcgacaac | ctctgggccg | agtccaagag | atcccgcaag | 420 |
| tcgctcctgc | ccgcatgggg | cttacagaac | ctgaaaggcg | catttgaaa | aagagttgca | 480 |
| gaaacagttc | atggaagctt | aagcttcgtt | cagcttccct | tggccccct | ggctgctcgg | 540 |

```
gcccggatcg cggaccgggg cgtttccggg gatttctgaa gcggacgagg ggcagggcgg    600
gcgaaggcca ttcggctctc cttctggctc cagaatctcc caacccgcag gtgtgcagtg    660
tgaccagcgc gactcaccgc tctaatcgct ccgattttcc aaggccttgc tcagtagtcc    720
tgccaggcgg gctctgaggc tggaaggat tggggagttc ggtgagtgcg ccctgcctat    780
agcgcccagt ggaatcgcta gtacctgtct ctgtggcgca atcggtcaga gcgttcggct    840
attaaccgaa cggtgagtag ttcaagacca cccaggacg cctgttctag ctttttttaa    900
agcattcatg tattatcatc actagagaat ctcccctat tcttcccata gtcctaagtc    960
cgaaaggttg gttccaggcc agcggcgcgc cgctagcaga tct                   1003
```

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5

```
gctaacgccg tggccggtg                                                  19
```

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6

```
gctaacgccg tggccggtg                                                  19
```

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7

```
tcgctagtac ctgtctctgt gg                                              22
```

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8

```
cctgggtggt cttgaactac tc                                              22
```

<210> SEQ ID NO 9
<211> LENGTH: 324
<212> TYPE: DNA
<213> ORGANISM: Schizosaccharomyces pombe

<400> SEQUENCE: 9

```
ggatcctttt cgttcaatca agatatttta tcacattatt tcaaggttca atgaatcatt    60
cgaagaatag taacgaattc agatatatta aataaaggca cacataatct ctaaagatta   120
cagtttaatg gctctttcaa agtgtttagt aatatataca ctaaatttct aaaattcagt   180
```

```
agttatggcg aagtggccga gtggtctatg gcgctagctt caggtgaaag caattgctag      240
tctacgtatg tgggcgtggg ttcgaacccc accttcgtca atataatttt ttatatcatg      300
ttaatggaat tgagaaaaac tagt                                             324

<210> SEQ ID NO 10
<211> LENGTH: 299
<212> TYPE: DNA
<213> ORGANISM: Homo sapiens

<400> SEQUENCE: 10
gccgggcgcg gtggcgcgtg cctgtagtcc cagctactcg ggaggctgag gctggaggat       60
cgcttgagtc caggagttct gggctgtagt gcgctatgcc gatcgggtgt ccgcactaag      120
ttcggcatca atatggtgac ctcccgggag cgggggacca ccaggttgcc taaggagggg      180
tgaaccggcc caggtcggaa acggagcagg tcaaaactcc cgtgctgatc agtagtggga      240
tcgcgcctgt gaatagccac tgcactccag cctgggcaac atagcgagac cccgtctct      299
```

RECOMBINANT PROTEIN PRODUCTION

CROSS REFERENCE TO RELATED APPLICATIONS

This is the U.S. National Stage of International Application No. PCT/GB2017/050028, filed Jan. 9, 2017, which was published in English under PCT Article 21(2), which in turn claims the benefit of GB 1600512.6, filed Jan. 12, 2016.

FIELD OF THE INVENTION

The disclosure relates to recombinant protein expression systems comprising genetically modified cells wherein the cells are transformed or transfected with tRNA genes to reduce base mismatch due to genetic degeneracy in the genetic code and hence reliance on wobble for decoding; the modified cells have so improved recombinant protein expression.

BACKGROUND TO THE INVENTION

The amino acid composition of proteins determines their properties and is encoded by the DNA sequence of genes. The gene sequence is copied into messenger RNA (mRNA) and decoded using transfer RNA (tRNA) that delivers amino acids in the specified order. The code is written in contiguous triplets of bases, called codons and is decoded by binding to the tRNAs' complementary base triplets, called anticodons. Each tRNA has a single anticodon and delivers a specified amino acid. However, although the combination of the four bases present in the DNA provides 64 codons, there are fewer tRNAs and anticodons present.

DNA comprises four different bases whereby adenosine specifically binds with thymine and guanine specifically binds with cytosine. All organisms have fewer species of tRNA than codons and therefore some tRNA species must pair with more than one codon, which led to the "Wobble" hypothesis postulating that the 5' base on the anticodon, which binds to the 3' base on the mRNA, can have non-standard base pairing, with only two of the three bases optimally matched. Suboptimal base pairing can lead to misincorporation errors upon translation. The most frequent errors correspond to a G (mRNA)/U (tRNA) base pair mismatch and additional wobble position mismatches (C/U and U/U) during translation.

Heterologous expression of recombinant proteins provided a wealth of diagnostic and therapeutic agents. Often bacterial systems are the preferred host for protein expression due to the low maintenance and easy handling. However, inability to accommodate for posttranslational modifications led to the usage of other expression systems such as yeast, insect cells, plants or mammalian expression systems. Approximately 70% of recombinant protein pharmaceuticals and most proteins used for vaccination, human therapy or diagnostics are currently produced in mammalian cells or cell lines, such as CHO or HEK293. However, although the choice of expression systems aids expression, there are still significant misincorporation levels being reported when expressing therapeutic monoclonal antibodies in CHO cells during clinical development. The impact of such sequence variation affects not just the quality and efficacy, but could compromise patient safety by triggering an immunogenic response.

Optimal protein expression systems leading to error-free and soluble protein expression are highly desired. As described above, no organism harbours a full set of tRNAs and moreover, there are species-dependent differences. Expression of e.g. a human-derived transgene in a bacterial system is often problematic, as the codon usage and frequency can differ greatly, leading to inefficient expression. This problem is generally addressed by optimising codons to the preferred codon usage by the expression hosts. However, manipulating transgene sequence is extremely problematic, as it interferes with the structure, folding, stability and regulation of the encoded mRNA transcript in ways that are poorly understood and highly unpredictable. An alternative approach is to introduce additional tRNA transgenes into the host so as to improve codon recognition; this has been used successfully in *E. coli*, but has not been attempted in eukaryotic hosts. In addition this approach does not deal with the problems associated with wobble such as inefficient translation and reduced translational fidelity.

The present disclosure relates to the introduction of tRNA genes with anticodons to optimally match codons that otherwise depend on wobble; in this way, unintended heterogeneity can be reduced and efficiency of protein synthesis can be improved.

STATEMENT OF THE INVENTION

According to an aspect of the invention there is provided an isolated eukaryotic cell wherein the cell is modified by transfection or transformation with a nucleic acid molecule comprising a transcription cassette, the transcription cassette comprising at least one nucleotide sequence encoding a transfer RNA [tRNA], the tRNA including an anticodon nucleotide sequence that is absent from said eukaryotic cell, wherein said anticodon sequence corrects base mismatches at any one of the cognate first, second or third nucleotide position in the corresponding messenger RNA [mRNA] codon to improve translation efficiency and/or decrease amino acid mis-incorporation as a consequence of degeneracy in the genetic code.

In an alternative aspect of the invention said cell is a prokaryotic cell.

In a preferred embodiment of the invention said base mismatch correction reduces said cells reliance on wobble during translation of said mRNA.

"Wobble" is a well-known natural phenomenon. The genetic code means that a cell would need tRNAs with 61 different anticodons to complement the available 61 codons. However, due to the degeneracy of the genetic code, the third base is less discriminatory for the amino acid than the other two bases. This third position in the codon is referred to as the "wobble" position. At this position Us and Cs may be read by a G in the anticodon. Similarly, As and Gs may be read by a U or y (pseudouridine) in the anticodon, and A, U or C can be read by inosine in the anticodon. This flexibility in codon recognition can result in less efficient translation and potential mis-incorporation of amino acids. The invention addresses these problems by genetically engineering cells to reduce the reliance on "wobble" to enhance translation and increase translation fidelity. The transcription cassette according to the invention is adapted for expression of said tRNA. This includes the provision of a suitable RNA polymerase III promoter. Alternatively, the transcription cassette can be intergrated into the genome of said cell at a position near to a suitable promoter, for example an RNA polymerase III promoter.

In a preferred embodiment of the invention said tRNA corrects a base mismatch in the first, second or third nucleotide position in the corresponding mRNA codon.

In a preferred embodiment of the invention said nucleic acid molecule is part of an expression vector adapted for eukaryotic expression of said tRNA.

In a preferred embodiment of the invention said cell is further modified by transformation or transfection with a nucleic acid molecule encoding a recombinant protein, polypeptide or peptide.

In a preferred embodiment of the invention said expression vector is adapted for expression in a mammalian cell.

Typically, said adaptation includes the provision of transcription control sequences (promoter sequences) which mediate cell/tissue specific expression. These promoter sequences may be cell/tissue specific, inducible or constitutive. "Promoter" is an art recognised term and, for the sake of clarity, includes the following features which are provided by example only. Enhancer elements are cis acting nucleotide sequences often found 5' to the transcription initiation site of a gene (enhancers can also be found 3' to a gene sequence or even located in intronic sequences). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors is responsive to a number of physiological/environmental cues which include, by example and not by way of limitation, intermediary metabolites (e.g. glucose, lipids), environmental effectors (e.g. heat). Promoter elements also include so called TATA box and RNA polymerase initiation selection sequences which function to select a site of transcription initiation. These sequences also bind polypeptides which function, inter alia, to facilitate transcription initiation selection by RNA polymerase II or III. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

Adaptations also include the provision of selectable markers and autonomous replication sequences which facilitate the maintenance of said vector in either the eukaryotic cell or prokaryotic host. Vectors which are maintained autonomously are referred to as episomal vectors. Episomal vectors are desirable since these molecules can incorporate large DNA fragments (30-50 kb DNA). Episomal vectors of this type are described in WO98/07876. Alternatively, vectors can be "integrating vectors" which recombine with chromosomal DNA to stably transform the cell into which the integrating vector is incorporated.

Adaptations which facilitate the expression of vector encoded recombinant genes include the provision of transcription termination/polyadenylation sequences. This also includes the provision of internal ribosome entry sites (IRES) which function to maximise expression of vector encoded genes arranged in bi-cistronic or multi-cistronic expression cassettes. Expression control sequences also include so-called Locus Control Regions (LCRs). These are regulatory elements which confer position-independent, copy number-dependent expression to linked genes when assayed as transgenic constructs. LCRs include regulatory elements that insulate transgenes from the silencing effects of adjacent heterochromatin, Grosveld et al., Cell (1987), 51: 975-985. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

Additionally, a number of viruses are commonly used as vectors for the delivery of exogenous genes. Commonly employed vectors include recombinantly modified enveloped or non-enveloped DNA and RNA viruses, preferably selected from baculoviridiae, parvoviridiae, picornoviridiae, herpesveridiae, poxviridae, adenoviridiae, or picornnaviridiae. Chimeric vectors may also be employed which exploit advantageous elements of each of the parent vector properties (See e.g., Feng, et al. (1997) Nature Biotechnology 15:866-870). Such viral vectors may be wild-type or may be modified by recombinant DNA techniques to be replication deficient, conditionally replicating or replication competent.

In a preferred embodiment of the invention said expression vector is adapted for expression in a fungal cell.

In a preferred embodiment of the invention said expression vector is adapted for expression in an insect cell.

In a preferred embodiment of the invention said expression vector is adapted for expression in a plant cell.

Suitable promoters for expression of recombinant proteins or tRNAs in plant cells include constitutive, tissue-specific, inducible, developmental or other promoters for expression in plant cells. Such promoters include viral, fungal, bacterial, animal and plant-derived promoters capable of functioning in plant cells. Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18 (675-689); pEMU (Last et al. (1991) Theor Appl. Genet. 81: 581-588); MAS (Velten et al. (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142, each of which is incorporated by reference.

Chemical-regulated plant promoters can be used to modulate the expression of a gene in a plant cell through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art of plant transgenic expression and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated plant promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevasoni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

Particular of interest in the present context are nucleic acid constructs which operate as plant vectors. Specific procedures and vectors previously used with wide success in plants are described by Guerineau and Mullineaux (1993) (Plant transformation and expression vectors. In: Plant Molecular Biology Labfax (Croy R R D ed) Oxford, BIOS Scientific Publishers, pp 121-148. Suitable vectors may include plant viral-derived vectors (see e.g. EP194809). If desired, selectable genetic markers may be included in the construct, such as those that confer selectable phenotypes such as resistance to herbicides (e.g. kanamycin, hygromycin, phosphinotricin, chlorsulfuron, methotrexate, gentamycin, spectinomycin, imidazolinones and glyphosate).

In a preferred embodiment of the invention said isolated eukaryotic cell is an insect, plant, fungal or mammalian cell.

In a preferred embodiment of the invention said isolated mammalian cell is a non-human mammalian cell.

In a further preferred embodiment of the invention said isolated mammalian cell is selected from the group consisting of: Chinese Hamster Ovary, [CHO], HEK293, NS0 or CAP cells.

In a further preferred embodiment of the invention said fungal cell is selected from the group consisting of yeast: *Saccharomyces cerevisae, Schizosaccharomyces pombe Pichia pastoris, Aspergillus* spp [e.g *A. niger*], *Kluyveromyces lactis* and *Trichoderma reesei* and *Yarrowia lipolytica.*

In a preferred embodiment of the invention said plant cell is isolated from a plant species selected from the group: corn (*Zea mays*), canola (*Brassica napus, Brassica rapa* ssp.), alfalfa (*Medicago sativa*), rice (*Oryza sativa*), rye (*Secale cerale*), Sorghum (*Sorghum bicolor, Sorghum vulgare*), sunflower (*helianthus annuas*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Preferably, plant cells of the present invention are crop plants (for example, cereals and pulses, maize, wheat, potatoes, tapioca, rice, Sorghum, millet, cassava, barley, pea, and other root, tuber or seed crops). Important seed crops are oil-seed rape, sugar beet, maize, sunflower, soybean, and Sorghum. Horticultural plants to which the present invention may be applied may include lettuce, endive, and vegetable brassicas including cabbage, broccoli, and cauliflower, and carnations and geraniums. The present invention may be applied in tobacco, cucurbits, carrot, strawberry, sunflower, tomato, pepper, *chrysanthemum*. Grain plants that provide seeds of interest include oil-seed plants and leguminous plants. Seeds of interest include grain seeds, such as corn, wheat, barley, rice, *Sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea.

In a further preferred embodiment of the invention said expression cassette comprises nucleotide sequences encoding 1, 2, 3, 4, 5, 6, 7, 8, 9, 10, 11, 12, 13, 14 or 15 different tRNAs.

In an embodiment of the invention said nucleic acid encodes a transfer RNA selected from the group of Ala-tRNA, Arg-tRNA, Asp-tRNA, Asn-tRNA, Cys-tRNA, Glu-tRNA, Gln-tRNA, Gly-tRNA, His-tRNA, Ile-tRNA, Leu-tRNA, Lys-tRNA, Met-tRNA, Phe-tRNA, Pro-tRNA, Ser-tRNA, Thr-tRNA, Trp-tRNA, Tyr-tRNA and Val-tRNA.

In a preferred embodiment said anticodon is cytosine and/or adenine rich.

In a preferred embodiment said anticodon is uracil free.

In a further preferred embodiment said anticodon is selected from the group consisting of AGC, GGC, CGC, UGC, ACC, GCC, CCC, UCC, AGG, GGG, CGG, UGG, AGU, GGU, CGU, UGU, AAC, GAC, CAC, UAC, AAA, GAA, AUU, GUU, CUU, UUU, AUC, GUC, CUC, UUC, AGA, GGA, CGA, UGA, ACU, GCU, ACG, GCG, CCG, UCG, CCU, UCU, AAG, GAG, CAG, UAG, CAA, UAA, AAU, GAU, UAU, CAU, AUA, GUA, ACA, GCA, AUG, GUG, CUG, UUG, CCA In a preferred embodiment of the invention said modified cell is transformed or transfected with a nucleic acid molecule encoding a therapeutic antibody.

In an alternative embodiment of the invention said modified cell is transformed or transfected with a nucleic acid molecule encoding a pharmaceutical or therapeutic protein or peptide.

In a further preferred embodiment of the invention said modified cell is transformed or transfected with a nucleic acid molecule encoding an industrial enzyme.

In a preferred embodiment of the invention said modified cell is further modified by transformation or transfection with a nucleic acid molecule comprising a 7SL nucleotide sequence.

Secreted and membrane proteins contain signal sequences that are required to target proteins to be secreted to the endoplasmic reticulum. The signal sequences of native and recombinant proteins destined for secretion interact with a signal recognition particle which is a ribonucleoprotein complex comprising six different proteins and a structural RNA of around 300 nucleotides and is referred to as 7SL RNA. 7SL RNA is conserved across species and although there is little homology at the level of sequence identity the secondary structures of 7SL RNA are highly conserved comprising a central double stranded region which is flanked at one end by two small stem loop structures and at the other end by two relatively large stem loop structures. We disclose that co-expression of 7SL nucleic acid in our modified cells greatly enhances expression of recombinant protein.

In a preferred embodiment of the invention said nucleic acid molecule comprises the nucleotide sequence set forth in SEQ ID NO: 10, or a nucleotide sequence variant that has at least 90% nucleotide sequence identity over the full length to the nucleotide sequence set forth in SEQ ID NO: 10.

In a preferred embodiment of the invention there is provided a nucleic acid molecule that comprises a nucleotide sequence that has at least 91%, 92%, 93%, 94%, 95%, 96%, 97%, 98% or 99% nucleotide sequence identity over the full length to the nucleotide sequence set forth in SEQ ID NO: 10.

Preferably, said nucleic acid molecule comprises or consists of a nucleotide sequence as set forth in SEQ ID NO: 10.

In a preferred embodiment of the invention translation efficiency is enhanced by greater than 1-fold when compared to a non-modified cell of the same species.

In a preferred embodiment of the invention translation efficiency is enhanced at least two fold when compared to a non-modified cell of the same species.

Preferably, translational efficiency is enhanced at least 3-fold, 4-fold, 5-fold, 6-fold, 7-fold, 8-fold, 9-fold or at least 10-fold when compared to a non-modified cell of the same species. Preferably, translation is enhanced by greater than 10-fold when compared to a non-modified cell of the same species.

In a preferred embodiment of the invention the mis-incorporation of amino acids in said recombinant protein is suppressed by greater than 1-fold when compared to the amino acid mis-incorporation rate in a non-modified cell of the same species.

In a preferred embodiment of the invention the mis-incorporation of amino acids in said recombinant protein is suppressed by at least 2-fold when compared to the amino acid mis-incorporation rate in a non-modified cell of the same species.

Preferably, mis-incorporation is suppressed by at least 3-fold, 4-fold, 5-fold, 6-fold, 7-fold, 8-fold, 9-fold, 10-fold, 15-fold, 20-fold, 25-fold, 30-fold, 35-fold or at least 40-fold when compared to the amino acid mis-incorporation rate in a non-modified cell of the same species.

According to an aspect of the invention there is provided a modified cell according to the invention for use in reducing tRNA mismatch as a consequence of the degeneracy in the genetic code in the production of recombinant protein.

Preferably, said reduction in tRNA mismatch reduces said cell's reliance on wobble during translation of said mRNA by said modified cell.

According to a further aspect of the invention there is provided a method for reducing tRNA mismatch as a consequence of the degeneracy in the genetic code comprising the steps:
 i) providing a modified cell according to the invention;
 ii) incubating the cell in i) under cell culture conditions suitable for expression of one or more recombinant proteins/peptides expressed by said modified cell; and optionally
 iii) isolating the expressed recombinant proteins/peptides from the modified cell or cell culture medium.

According to a further aspect of the invention there is provided a method to customise expression of a selected recombinant protein in a cell expression system comprising the steps:
 i) analysing the nucleotide sequence of a nucleic acid molecule encoding a recombinant protein to be expressed to identify one or more codon/anticodon tRNA mismatches;
 ii) transfecting or transforming a cell with one or more transcription cassettes comprising one or more tRNA genes that correct at least one base pairing mismatch in at least one codon to provide a modified cell;
 iii) transfecting or transforming said modified cell with the recombinant protein to be expressed; and optionally
 iv) providing cell culture conditions to express said recombinant protein.

In a preferred method of the invention said cell is a eukaryotic cell.

Preferably, said cell is a mammalian cell, a fungal cell, an insect cell or a plant cell.

In an alternative preferred method of the invention said cell is a prokaryotic cell, for example a bacterial cell.

According to an aspect of the invention there is provided a modified cell obtained or obtainable by the method according to the invention.

According to a further aspect of the invention there is provided a cell culture vessel comprising a modified cell according to the invention. In a preferred embodiment of the invention said cell culture vessel is a bioreactor such as a fermenter.

If eukaryotic microbial or prokaryotic expression is preferred in the methods according to the invention they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batch wise, semi-batch wise or continuously. Nutrients can be provided at the beginning of the fermentation or fed in semi-continuously or continuously. Recombinant protein produced can be isolated from the organisms as described above by processes known to the skilled worker, for example by extraction, if appropriate precipitation with salt, and/or chromatography. To this end, the organisms can advantageously be disrupted beforehand.

In this process, the pH value kept between pH 4 and 12, preferably between pH 6 and 9, especially preferably between pH 7 and 8. The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements. Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron. Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine. Phosphoric acid, potassium dihydrogenphosphate or dipotassium hydrogenphosphate or the corresponding sodium-containing salts may be used as sources of phosphorus.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium.

According to a further aspect of the invention there is provided a method for the customised in vitro synthesis of recombinant protein comprising the steps:
  i) analysing the nucleotide sequence of nucleic acid molecule encoding a recombinant protein to be expressed to identify one or more codon/anticodon tRNA mismatches;
  ii) providing a reaction mixture comprising mRNA encoding said recombinant protein and one or more tRNAs that correct at least one base pairing mismatch in at least one codon in said mRNA; and
  iii) providing reaction conditions for the synthesis of said recombinant protein from said mRNA.

In a preferred method of the invention said reaction mixture includes an expression vector and RNA polymerase and the method is a combined transcription/translation reaction.

According to a further aspect of the invention there is provided a kit comprising:
  an expression vector[s] comprising one or more tRNA genes; optionally
  an expression vector adapted to receive one or more recombinant nucleic acid molecules; and
  enzymes and buffers required for sub-cloning and/or transfection/transformation.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

PREFERRED EMBODIMENTS

Antibodies include polyclonal, monoclonal antibodies, humanised and chimeric antibodies and derived fragments comprising CDRs.

Chimeric antibodies are recombinant antibodies in which all of the V-regions of a mouse or rat antibody are combined with human antibody C-regions. Humanised antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

Various fragments of antibodies are known in the art. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A $Fab_2$ fragment comprises two joined Fab fragments. When these two fragments are joined by the immunoglobulin hinge region, a $F(ab')_2$ fragment results. An Fv fragment is multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, *Fundamental Immunology* or Janeway et al. *Immunobiology* (cited above). Molecular biology now allows direct synthesis (via expression in cells or chemically) of these fragments, as well as synthesis of combinations thereof. A fragment of an antibody or immunoglobulin can also have bispecific function as described above.

Pharmaceutical Proteins & Peptides

Examples of pharmaceutical proteins include "cytokines". Cytokines are involved in a number of diverse cellular functions. These include modulation of the immune system, regulation of energy metabolism and control of growth and development. Cytokines mediate their effects via receptors expressed at the cell surface on target cells. Examples of cytokines include the interleukins such as: IL1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and 33. Other examples include growth hormone, leptin, erythropoietin, prolactin, tumour necrosis factor [TNF] granulocyte colony stimulating factor (GCSF), granulocyte macrophage colony stimulating factor (GMCSF), ciliary neurotrophic factor (CNTF), cardiotrophin-1 (CT-1), leukemia inhibitory factor (LIF) and oncostatin M (OSM), interferon α, interferon β, interferon ε, interferon κ and ω interferon.

Examples of pharmaceutically active peptides include GLP-1, anti-diuretic hormone; oxytocin; gonadotropin releasing hormone, corticotrophin releasing hormone; calcitonin, glucagon, amylin, A-type natriuretic hormone, B-type natriuretic hormone, ghrelin, neuropeptide Y, neuropeptide $YY_{3-36}$, growth hormone releasing hormone, somatostatin; or homologues or analogues thereof.

The term "chemokine" refers to a group of structurally related low-molecular weight factors secreted by cells having mitogenic, chemotactic or inflammatory activities. They are primarily cationic proteins of 70 to 100 amino acid residues that share four conserved cysteine residues. These proteins can be sorted into two groups based on the spacing of the two amino-terminal cysteines. In the first group, the two cysteines are separated by a single residue (C-x-C) while in the second group they are adjacent (C-C). Examples of members of the 'C-x-C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and II (AMCF-1 and —II), pre-B cell growth stimulating factor (PBSF), and IP10. Examples of members of the 'C-C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1 α (MIP-1-α), macrophage inflammatory protein 1β (MIP-1-β), macrophage inflammatory protein 1-γ (MIP-1-γ), macrophage inflammatory protein 3 α (MIP-3-α, macrophage inflammatory protein 3 β (MIP-3-β), chemokine (ELC), macrophage inflammatory protein-4 (MIP-4), macrophage inflammatory protein 5 (MIP-5), LD78 β, RANTES, SIS-epsilon (p500), thymus and activation-regulated chemokine (TARC), eotaxin, 1-309, human protein HCC-1/NCC-2, human protein HCC-3.

A number of growth factors have been identified which promote/activate endothelial cells to undergo angiogenesis. These include vascular endothelial growth factor (VEGF A); VEGF B, VEGF C, and VEGF D; transforming growth factor (TGFb); acidic and basic fibroblast growth factor (aFGF and bFGF); and platelet derived growth factor (PDGF). VEGF is an endothelial cell-specific growth factor which has a very specific site of action, namely the promotion of endothelial cell proliferation, migration and differentiation. VEGF is a complex comprising two identical 23 kD polypeptides. VEGF can exist as four distinct polypeptides of different molecular weight, each being derived from an alternatively spliced mRNA. bFGF is a growth factor that functions to stimulate the proliferation of fibroblasts and endothelial cells. bFGF is a single polypeptide chain with a molecular weight of 16.5 Kd. Several molecular forms of bFGF have been discovered which differ in the length at their amino terminal region. However the biological function of the various molecular forms appears to be the same.

BRIEF SUMMARY OF THE DRAWINGS

An embodiment of the invention will now be described by example only and with reference to the following figures:

FIG. 8: Illustrates the percentage of Herceptin (trastuzumab) polypeptides secreted by matched clones of cells stably transfected with pCET1006L&H with or without pcDNA.YIN that have lysine erroneously incorporated instead of asparagine at residue 156 of the light chain and residues 307, 336 and 405 of the heavy chain;

MATERIALS AND METHODS

Figure 1:
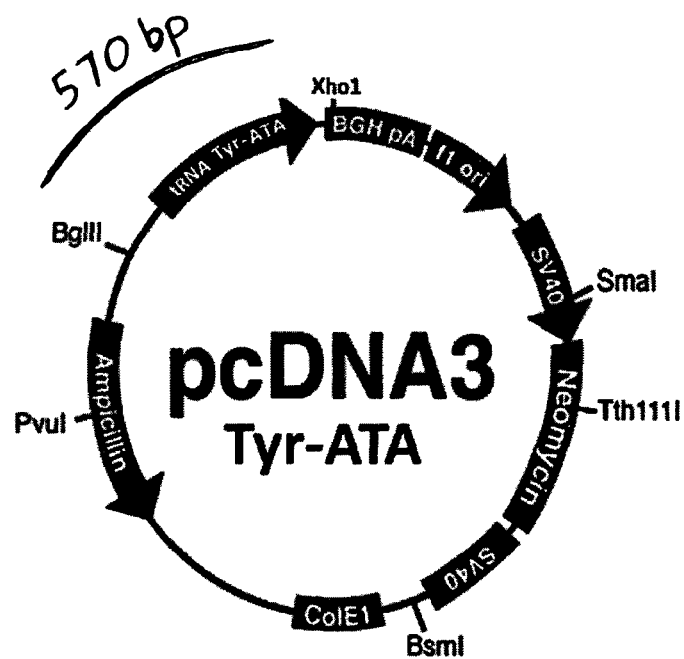
FIG. 1: Illustrates expression vector pcDNA3 Tyr-ATA carrying a 570 bp insert that includes a tRNA TyrATA gene that is absent from CHO cells.

Cloning a Human tRNA-Tyr-ATA Gene into pcDNA3

A 500 bp genomic DNA fragment (sequence ID NO 1) containing the human tRNA-Tyr-ATA gene (chr2: 219110270-219110770) with the addition of an attB sequence at the 5' end and flanked by BglII (5') and XhoI (3') restriction enzyme sequences was synthesised by Life Technologies and provided in the vector pMK-Tyr_ATA. The sequence was released by digestion with BglII and XhoI at 37° C. and gel purified. The eukaryotic expression vector pcDNA3 was digested with BglII and XhoI to remove the CMV promoter, and gel purified. The two DNA fragments were joined using T4 ligase (NEB) and introduced into chemically induced competent E. coli by heat shock for 1 minute at 42° C. Plasmid was subsequently isolated from the resulting carbenicillin resistant (50 µg/ml) colonies and the presence of the insert confirmed by restriction digest and subsequent sequencing.

```
SEQ ID NO 1:
>chr2:219110270-219110770

BglII    NotI
TTAGATCTGCGGCCGCGTGAGCAGGGTGCACTTGCTGCTTT

TGTGCCGCTTTAATGAGTTCACACAGCAGAATACCTAAATC

TGCACAGAACCTTGGTTAACATTTTAAGGTAGGCAAACGC

AGGCATACCAACTTGTTCCTGTTGCCATTGCAGTGACTA

AAGGAGGGATGTCACAGGGTATTAATTACAGAGCAGGCCA

TATGCTATTTTTGTACAGTAATCCTTTCCTTTTTTTCCCC

ATTTTTCTTAAATCTTAAAAATAAGACTGAATTCTGATAT

CAAGAGTTAAGGTCCCTTCAATAGTTCAGCTGGTAGAGCAG

AGGACTATAGCTACTTCCTCAGTAGGAGACGTCCTTAGGTTG

CTGGTTCGATTCCAGCTTGAAGGAGACAAGTACAGTTTTGGCT

GGGCACGGTGGTTCATGGCTGTAATCACAGCACTTTGGGAGGTT

AAGGCAGGTGGATCACGAGGTCAGGAGATCAAGATCATCCTGG

CCAATGTGGTGAAACTCTGTCTCCGGTGCGGGTGCCAGGGCGTG

CCCTTGGGCTCCCCGGGCGCGTACTCCACGGGGCGGCCTCGAGTT
    attB                              NotI  XhoI
```

Sequence 1—Sequence of synthesised genomic fragment containing the human Tyr-ATA gene (green text) with the lambda Attb integration site fused at the 3' end for targeted genomic integration (yellow highlight).

Transfection of pcDNA-Tyr-ATA into CHO Cells

CHO-KI cells were grown in Ham's F12 media supplemented with 10% foetal calf serum and cultured at 37° C. in 5% $CO_2$. For transfection, 350,000 cells were plated per well in a 6 well plate containing 3 ml of media. The next day the media was removed and replaced by 1 ml fresh media and 5 µg of plasmid was introduced to the cells using the X-fect reagent (Clontech) according to the manufacturer's instructions. After 24 hrs, all cells from 3 wells were collected and re-plated into a T75 flask containing 15 ml media supplemented with 400 µg/ml G418 as the pcDNA vector carries a neomycin resistance gene. These cells were split 1:4 three days later and the G418 increased to 600 µg/ml. The cells were subsequently split 1:4 every 2-3 days and the G418 increased further to 800 µg/ml at day 12. Selection was continued at 800 µg/ml until no further cell death occurred, indicating fully transformed and resistant cell lines. Untransformed cells cultured in the presence of G418 did not expand and steadily dwindled in number.

Expression Analysis of pcDNA-Tyr-ATA

RNA was extracted from CHO cells using 1 ml/well Trizol (Life technologies) according to the manufacturer's instructions. Following precipitation, the RNA pellet was suspended in 30µ; 1× DNase1 buffer containing 4u RNase free DNase1 (NEB M0303S), the RNA was incubated at 37° C. for 30 min before stopping the reaction at 70° C. for 10 minutes. 1 µg of RNA was then reverse transcribed to cDNA using SuperScript IV (Life Technologies) and random nonomers (Sigma) as follows [mix 1 µg of RNA, 1 µl random nonomers, 1 µl 10 mM dNTP mix, RNase free water to 14 µl, heat to 70° C. for 5 min then chill on ice, add 4 µl 5×SSIV buffer, 1 µl 100 mM DTT and 1 µl SuperScript IV reverse transcriptase, leave to stand at room temperature for 10 min, then 55° C. for 30 min before stopping the reaction at 80° C. for 10 min]. The cDNA was subsequently diluted to 100 µl with DNase/RNase free water and was used in PCR reactions with OneTaq polymerase 2× mix (NEB) and gene-specific primers (SEQ ID NO 2: ATA forward—GCTGGTAGAGCAGAGGACTAT, SEQ ID NO 3: ATA(2) reverse—TCGAACCAGCAACCTAAGGAC). [OneTaq 2× with standard buffer—10 µl, cDNA—2 µl, 10 µM primers—0.2 µl, $dH_2O$ to 20 µl]. PCR conditions—[94° C.—3 min, (94° C.—30 s, 62° C.—12 s, 68° C.—12 s)×35, 68° C.—3 min] The results of the PCR were visualised on 3% TBE Agarose gel with SYBR Safe DNA stain (Invitrogen).

Construction of YIN Cluster of Human tRNA Genes (tRNA-IleGAT1-1, tRNA-AsnATT1-1 and tRNA-TyrATA).

Figure 3:
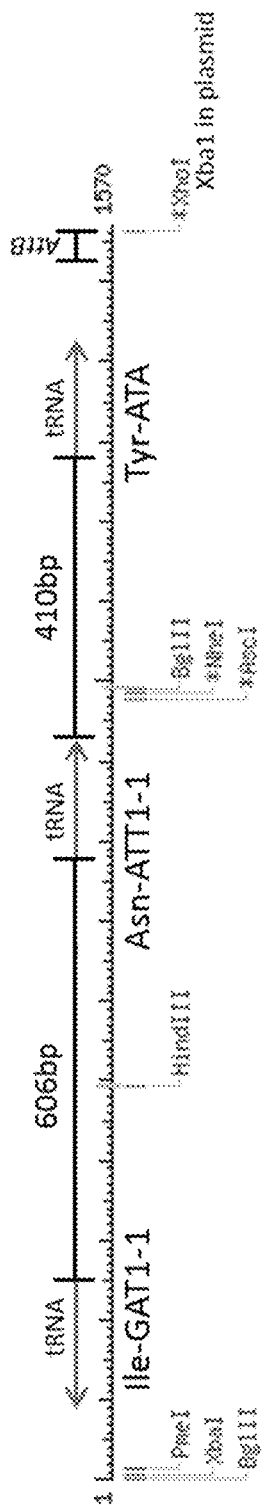
FIG. 3: Illustrates a transgenic cluster carrying three human tRNA genes with no equivalent in the CHO genome. These were incorporated cloned into pcDNA3 to create pcDNA.YIN, and stably transfected into CHO cells.

Sequence was obtained for each tRNA gene as follows—Ile-GAT 1-1 hg19_dna range ChrX: 3756418-3756491, Asn-ATT1-1 hg19_dna range chr1: 147718729-147719202. The sequences were synthesised as one fragment of DNA with HindIII site separating them (sequence ID NO 4), and flanked by BamHI sites for cloning adjacent to the Tyr-ATA tRNA sequence in pcDNA-Tyr-ATA (FIG. 3). The resultant construct was named pcDNA.YIN.,

```
SEQ ID NO 4:
BamHI / XbaI / PmeI

AGATCTTCTAGAGTTTAAACCGCCGCTCACAGTACCCGAAAGGCGCATTT

TTCACAAACTGTTGTAGAAAGAGTTCATGGCGGGTGGCGGCGGGAAAAA

AAAAAAAAAAGCTAACGCCGTGGCCGGTGCGGGAGTCGAGCCCGCGACCT

TGGTGTTATCAGCACCACGCTCTTACCAACTGAGCTAACCGGCCGCCTG

ACGGCACAGTGCCCCTGGAGCGTATAAAAGGGCTCCACGTTCGCGCCCGT

CCACGAGCGATTCCTCGCCAAGCCCGCGCGCCTCTGGCTGCCTTCCGC

TTTGCCCCAGCCGCGGGGACTCCGGGGAGGAGCCACCGCCCCAGCGCT

GGCCGGGTTTCTCCCGCTCCTCCCTGCCAGGCTGTCCTCGACAACCTC

TGGGCCGAGTCCAAGAGATCCCGCAAGTCGCTCCTGCCCGCATGGGGC

TTACAGAACCTGAAAGGCGCATTTTGAAAAAGAGTTGCAGAAACAGTT

CATGGAAGCTTAAGCTTCGTTCAGCTTCCCTTGGGCCCCCTGGCTGCT

CGGGCCCGGATCGCGGACCGGGGCGTTTCCGGGGATTTCTGAAGCGGA

CGAGGGGCAGGGCGGGCGAAGGCCATTCGGCTCTCCTTCTGGCTCCAG
```

-continued

```
AATCTCCCAACCCGCAGGTGTGCAGTGTGACCAGCGCGACTCACCGCT

CTAATCGCTCCGATTTTCCAAGGCCTTGCTCAGTAGTCCTGCCAGGCG

GGCTCTGAGGCTGGAAGGGATTGGGGAGTTCGGTGAGTGCGCCCTGCC

TATAGCGCCCAGTGGAATCGCTAGTACCTGTCTCTGTGGCGCAATCGG

TCAGAGCGTTCGGCTATTAACCGAACGGTGAGTAGTTCAAGACCACCC

AGGGACGCCTGTTCTAGCTTTTXXXAAAGCATTCATGTATTATCATCA

CTAGAGAATCTCCCCCTATTCTTCCCATAGTCCTAAGTCCGAAAGGTTG

GTTCCAGGCCAGCGGCGCGCCGCTAGCAGATCT
    AscI / NheI / BamHI
```

Introduction of YIN tRNA Gene Cluster into CHO Cells and Confirmation of Expression.

pcDNA-YIN was transfected stably into CHO K1 cells, as described above for pcDNA-Tyr-ATA. Expression of each tRNA was confirmed in transfectants (FIG. 4), as described above for tRNA-Tyr-ATA. Primer sequences were (SEQ ID NO 5: Forward-TCAGGCGGCCGGTTAGC, SEQ ID NO 6: Reverse—GCTAACGCCGTGGCCGGTG) for tRNA-Ile-GAT and (SEQ ID NO 7 Forward—TCGCTAGTACCTGTCTCTGTGG and SEQ ID NO 8: Reverse—CCTGGGTGGTCTTGAACTACTC) for tRNA-Asn-ATT.

Creation of Stably-Transfected Clones Expressing Herceptin (Trastuzumab)

One day prior to the transfection, 3×10$^5$ CHO cells were plated in 1 ml of complete growth medium (F12/DMEM) in 6-well Costar clear TC treated cell culture plates (Corning) so that the cells were 50-70% confluent at the time of transfection. In a microcentrifuge tube, 5 µg of plasmid pCET1006L+H (FIG. 5) DNA encoding Herceptin (trastuzumab) was diluted with Xfect Reaction Buffer to a final volume of 100 µl and mixed by vortexing for 5 sec at high speed. 1.5 µl Xfect Polymer was added to the diluted plasmid DNA, mixed well by vortexing for 10 sec at high speed (the ratio of Polymer:DNA held constant: 0.3 µl of Xfect Polymer per 1 µg of plasmid DNA). The mixture was incubated for 10 min at room temperature to allow nanoparticle complexes to form. The entire 100 µl of nanoparticle complex solution was added dropwise to the cell culture medium in a well. Plates were incubated at 37° C., 5% $CO_2$ for 4 hr to overnight, then nanoparticle complexes were removed from cells by aspiration, replaced with 2-3 ml fresh complete growth medium and the plates were returned to the 37° C. incubator. After 24 hrs, the cells were trypsinised, counted and resuspended at 200, 500 or 1000 cells/ml in ClonaCell™ semi-solid media (Stem Cell Technologies) supplemented with Glutamax (Gibco) and puromycin (10 µg/ml) in untreated plates. The plates were incubated at 37° C., 5% $CO_2$ for 14-21 days until the colonies were clearly visible. Individual colonies were pipetted off into liquid F12 media, supplemented with 10% FCS and 10 ug/ml puromycin, and expanded, before analysis by Western blot.

To assay expression of Herceptin (trastuzumab), 1 ml of medium was removed to an Eppendorf tube and spun at 1200 rpm to pellet any cellular debris. Supernatant (880 µl) was taken off and frozen at −80° C. Samples of medium (30 µl) were mixed with 10 µl alkylating loading buffer, (125 mM Tris, 20% glycerol 2% SDS, 90 mM N-Ethylmaleimide (NEM) Bromophenol blue) and incubated at RT for 15 mins. Samples were then heated at 95° C. for 10 mins and cooled on ice before SDS-PAGE. Protein was transferred to membrane (Amersham Protran 0.45 micron NC #10600003) pre-soaked in transfer buffer (Towbin-25 mM Tris-HCl, 192 mM Glycine, pH8.3, 20% MeOH) using a Hoefer Semiphor semi-dry blotter. The membrane was rinsed in 1×PBS and blocked O/N at 4° C. in 5% milk powder, 1% PVP-40 (Sigma 101616021), 0.05% Tween-20 (Applichem GmbH A4974) in 1×PBS). Blocking buffer was then removed and replaced with an HRP conjugated anti-human IgG antibody at a dilution of 1/5000. (Abcam 97165 1 mg/ml Goat pAb to human IgG HRP) and incubated for 1 hr at RT with shaking. The membrane was then washed 3×10 mins in 1×PBS+ 0.05% Tween 20. Proteins were detected by adding #34087 Thermo Super-Signal Western Pico Chemi substrate. Excess reagent was removed and signal detected with a SynGene G box chemiimager with GeneSnap software. Membranes were then rinsed in 1×PBS and Fibronectin antibody Ab 2413 (Abcam) added at a 1/10000 dilution in blocking buffer or Sigma F6140 Fibronectin mouse monoclonal 1/4000 dilution blocked in 5% BSA (Sigma A7906) and incubated O/N at 4° C. Membranes then were washed 3×10 mins 1×PBS+0.05% Tween 20, then secondary antibody added in milk blocking buffer (Anti-rabbit IgG HRP 7074S Cell Signalling at a dilution of 1/5000 or anti-mouse HRP 1/5000 dilution #7076P2 Cell Signalling) and incubated 1 hr at RT with shaking.

Membrane was washed 3×10 mins in PBS/Tween and developed using high sensitivity substrate as above. Chemiimages were analysed using image J (https://imagej.nih.gov/ij/index.html).

Effects of Wobble Suppression by YIN on Expression of Herceptin (Trastuzumab)

Clones stably transfected with pCET1006L+H were used to test how expression of Herceptin (trastuzumab) responds to wobble suppression by transient or stable introduction of human tRNA-IleGAT1-1, tRNA-AsnATT1-1 and tRNA-TyrATA genes using pcDNA.YIN. CHO cells do not have these three tRNAs and therefore rely on wobble to decode ATC, AAT and TAT codons for Ile, Asn and Tyr, respectively.

Figure 6:
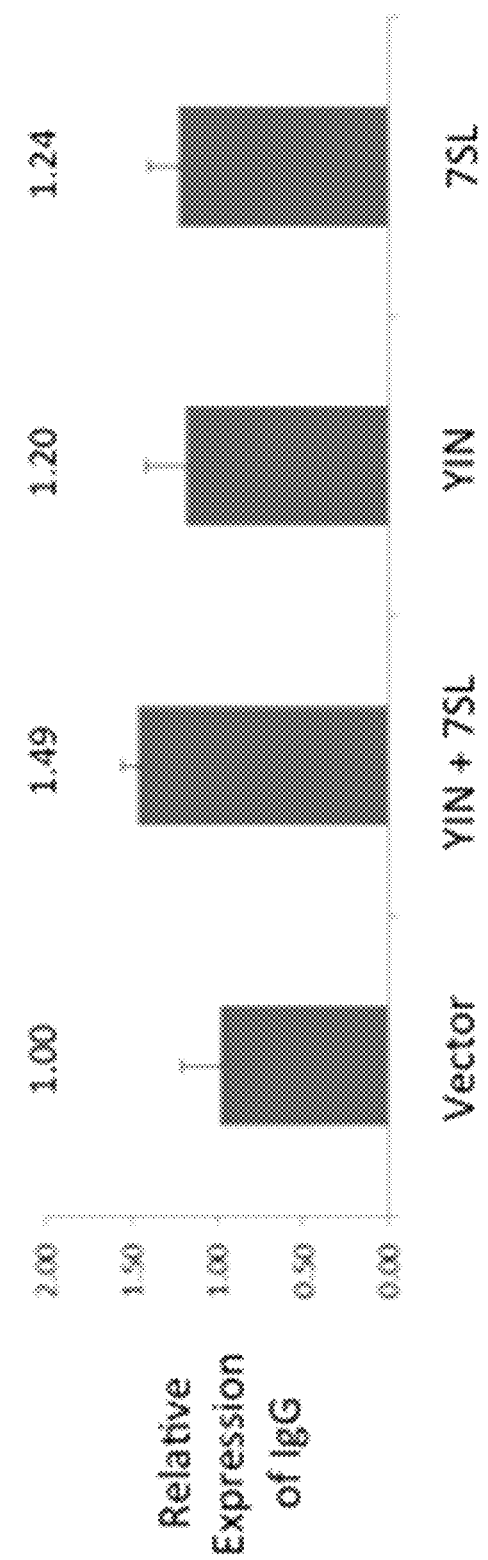
FIG. 6: Illustrates the effects on relative expression of secreted Herceptin (trastuzumab) of transiently transfecting cloned cells carrying stably incorporated pCET1006L&H with empty vector, pcDNA.YIN+pSUPER.7SL, pcDNA.YIN+vector, or pSUPER-7SL+vector. Mean relative expression (n=3) was vector 1.00, pcDNA.YIN+pSUPER-7SL 1.49, pcDNA.YIN+vector 1.20, pSUPER-7SL+vector 1.24.

Clones expressing stably transfected pCET1006L+H were grown at 37° C. in 5% $CO_2$ in Hams F12 medium with L-glutamine (Lonza BE12615F), supplemented with 10% foetal calf serum (Gibco 10270), 100 U/ml Pen/Strep (Gibco 15140122) and 10 µg/ml Puromycin (Gibco A11138) and transfected with pcDNA.YIN or equal amounts of pcDNA.3 empty vector, using Genecelin. Response to overexpression of 7SL RNA was tested in parallel, by cotransfection of pSUPER-7SL (Misra et al. (2005) J. Biol. Chem 280, 29364), with equal amounts of pcDNA.YIN or empty vector. Levels of Herceptin (trastuzumab) secreted into medium were determined by western blot, as above, 3 days after transfection (FIG. 6).

To test the effect of stably expressing tRNA-IleGAT1-1, tRNA-AsnATT1-1 and tRNA-TyrATA, clones stably transfected with pCET1006L+H were further transfected with pcDNA.YIN, as above. After 24 hrs, the cells were trypsinised, counted and resuspended at 200, 500 or 1000 cells/ml in ClonaCell™ semi-solid media (Stem Cell Technologies) supplemented with Glutamax (Gibco) and puromycin (10 µg/ml) (Gibco A11138), for continued selection of pCET1006L+H integration, and 800 µg/ml G418 (Sigma A1720) for selection of pcDNA.YIN integration. The plates were incubated at 37° C., 5% $CO_2$ for 14-21 days until the colonies were clearly visible. Individual colonies were pipetted off into liquid F12 media, supplemented with 10% FCS, 800 µg/ml G418 and 10 µg/ml puromycin, and expanded. These and parental clones were cultured in T25 cell culture flasks (Starsted) at 37° C. in 5% $CO_2$ in Hams F12 medium with L-glutamine (Lonza BE12615F), supplemented with 10% foetal calf serum (Gibco 10270), 100 U/ml Pen/Strep (Gibco 15140122) and 10 µg/ml Puromycin (Gibco A11138), with or without 800 µg/ml G418 (Sigma A1720), as appropriate. To assay expression of Herceptin (trastuzumab), 500,000 cells (at passages 4-8) were plated in 5 ml of medium in a T25 flask, as above. After 72 hrs, a 1 ml aliquot of medium was removed to an Eppendorf tube and spun at 1200 rpm to pellet any cellular debris. Supernatant (880 µl) was taken off and frozen at −80. Expression was assayed subsequently by western blot, as described above (FIG. 7).

Effects of Wobble Suppression on Misincorporation of Lysine for Asparagine in Herceptin (Trastuzumab)

For analysis by mass spectrometry (MS), Herceptin was purified from cell culture supernatant (F12:DMEM medium with 10% Ultra-Low IgG FBS [Thermo Scientific]) harvested 72-96 hr after plating of single cell clones of stably expressing CHO cells, using Pierce Protein A Magnetic Beads. (Thermo Scientific Pierce 50 µl, 0.5 mg) Magnetic Beads were pipetted to a microcentrifuge tube. The tube was placed on the magnet to separate the beads from the storage solution. The Magnetic Beads were washed with 1 ml wash buffer (TBS containing 0.05% Tween-20 Detergent), the beads were collected by magnet and the supernatant removed. 30 ml of the cell culture supernatant was concentrated to 1.5 ml using Amicon Ultra-15 Centrifugal Filter Units with Ultracel-50 membrane (Merck Millipore), added to the beads and incubated with rotation for 60 min at room temperature. The tube was placed on the magnet and the supernatant removed. The beads/antibody complex was resuspended in 500 µl wash buffer and washed by gentle pipetting. The beads/antibody complex was washed in total 3 times and separated on the magnet between each wash. The bead suspension was transferred to a clean tube to avoid co-elution of proteins bound to the tube wall. 100 µl of elution buffer (50 mM glycine pH 2.8) was added to the beads for 10 min to elute the antibody and the buffer was neutralised by adding 15 µl 1M TRIS pH 7.5. The eluted protein was mixed with LDS sample buffer (Biorad, 4:1) and reduced by DTT (final concentration 100 mM). The mixture was heated for 10 min at 95° C. and loaded onto a 4-15% SDS-PAGE gel (Biorad). The gel was run according to the manufacturer's instructions (180V, 30-40 min). The SDS-PAGE gel was stained using InstantBlue Coomasie-based protein stain (Expedeon). In-gel tryptic digestion was performed after reduction with DTE and S-carbamidomethylation with iodoacetamide. Gel pieces were washed twice with 50% (v:v) aqueous acetonitrile containing 25 mM ammonium bicarbonate, then once with acetonitrile and dried in a vacuum concentrator for 20 min. Sequencing-grade, modified porcine trypsin (Promega) was dissolved in 50 mM acetic acid, then diluted 5-fold with 25 mM ammonium bicarbonate to give a final trypsin concentration of 0.02 µg/µL. Gel pieces were rehydrated by adding 25 µL of trypsin solution, and after 10 min enough 25 mM ammonium bicarbonate solution was added to cover the gel pieces. Digests were incubated overnight at 37° C. Peptides were extracted by washing three times with 50% (v:v) aqueous acetonitrile containing 0.1% trifluoroacetic acid (v:v), before drying in a vacuum concentrator and reconstituting in aqueous 0.1% trifluoroacetic acid (v:v). Peptides were loaded onto an UltiMate 3000 RSLCnano HPLC system (Thermo) equipped with a PepMap 100 Å $C_{18}$, 5 µm trap column (300 µm×5 mm, Thermo) and an Acclaim PepMap RSLC or EasyNano column, 2 µm, 100 Å, ($C_{18}$, 75 µm×150 mm, Thermo). The trap wash solvent was aqueous 0.05% (v:v) trifluoroacetic acid and the trapping flow rate was 15 µl/min. The trap was washed for 3 min before switching flow to the capillary column. The separation used a gradient elution of two solvents (solvent A: aqueous 1% (v:v) formic acid; solvent B: aqueous 80% (v:v) acetonitrile containing 1% (v:v) formic acid). The flow rate for the capillary column was 300 nl/min. Column temperature was 40° C. and the gradient profile was: linear 3-10% B over 7 mins, linear 10-35% B over 30 mins, linear 35-99% B over 5 mins then proceeded to wash with 99% solvent B for 4 min. The column was returned to initial conditions and re-equilibrated for 15 min before subsequent injections.

The nanoLC system was interfaced with an Orbitrap Fusion hybrid mass spectrometer (Thermo) with a Nanospray Flex or EasyNano ionisation source (Thermo). Positive ESI-MS and $MS^2$ spectra were acquired using Xcalibur software (version 4.0, Thermo). Instrument source settings were: ion spray voltage, 1,900-2,400 V; sweep gas, 2 Arb; ion transfer tube temperature; 275° C. $MS^1$ spectra were acquired in the Orbitrap with common acquisition parameters among all acquisitions, specifically: 120,000 resolution; scan range, m/z 375-1,500; AGC target, $4e^5$; max fill time, 100 ms and data type, profile. $MS^2$ spectra were acquired in top speed mode maintaining a fixed cycle time of 1 s; quadrupole isolation window, m/z 1.6; activation type, HCD; collision energy, 32%; first mass, m/z 110 and data type, centroid. To maximise peptide identifications, multiple $MS^2$ acquisition regimes were performed using both the linear ion trap and Orbitrap mass analysers. Linear ion trap $MS^2$ acquisitions specified scan rate, rapid; AGC target, $5e^3$ and max injection time, 100 ms. Orbitrap $MS^2$ acquisitions used resolution, 30,000; AGC target, $5e^4$ and max injection time, 54 ms. Data dependent precursor selection was selected either the most or least (separate acquisitions) intense precursor above a threshold of $5e^3$. Dynamic exclusion was applied for 50 s post precursor selection and a minimum threshold for fragmentation was set at $5e^3$. Latterly, a targeted approach was taken for $MS^2$ acquisitions using a fixed inclusion list containing the theoretical 2+ and 3+m/z values for peptides previously identified as containing Asn to Lys modification.

Peak lists were generated in MGF format using MSConvert (proteowizard, version 3.0.9967). MGF files were searched against the expected protein sequences, appended to an in-house database, using a locally-running copy of the Mascot program (Matrix Science Ltd., version 2.5.1). Search criteria specified: Enzyme, semi-trypsin; Fixed modifications, Carbamidomethyl (C); Variable modifications, Oxidation (M), Asn→Lys (N); Peptide tolerance, 3 ppm; MS/MS tolerance, 0.5 Da for linear ion trap or 10 mDa for Orbitrap; Instrument, ESI-TRAP or ESI-ORBITRAP-HCD. Peptides classified as containing amino acid substitutions were required to have expect scores <0.05 and were manually validated to ensure the presence of sequence ions localising the position of substitution to the suggested amino acid.

Extracted ion chromatogram peak areas were generated using Qual Browser (Xcalibur, version 4.0, Thermo), setting a 2 mDa window around expected precursor m/z values. XICs were Gaussian smoothed and peak picking parameters specified: baseline window, 100; area noise factor, 5; peak noise factor, 100. Percentage of amino acid substitution was estimated by comparing the peptide XIC areas of the substituted form with the sum of the substituted and expected forms.

FIG. 8 shows the frequency of lysine misincorporation in matched clones with or without pcDNA.YIN. Data are given for four sites where misincorporation of lysine was detected consistently. In each case, the correct residue, asparagine, is encoded by an AAT codon that depends on wobble in native CHO cells, but can be decoded without wobble by tRNA-AsnATT in cells transfected with pcDNA.YIN.

Cloning a Fission Yeast tRNA-LeuCAG Gene into pRS426

Figure 9:
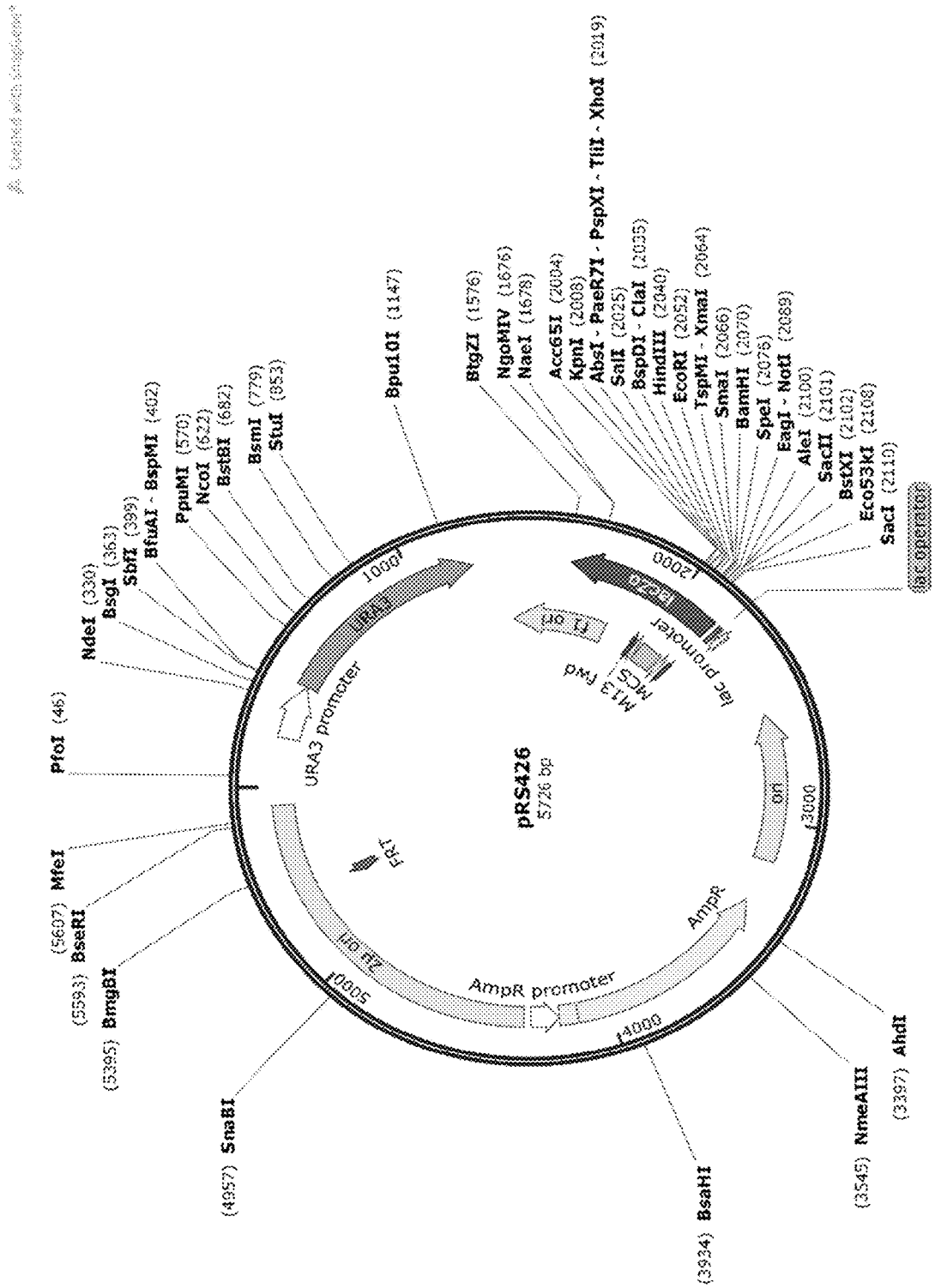
FIG. 9: Illustrates vector pRS426, which received a 300 bp fragment of *Schizosaccharomyces pombe* genomic sequence containing the tRNA49-LeuCAG gene (SEQ ID NO 9), to create pAU39.

A 300 bp fragment (sequence ID NO 9) of genomic DNA from chromosome I of the fission yeast *Schizosaccharomyces pombe* containing the tRNA49-LeuCAG gene (chr1: 1527350-1527050) flanked by BamHI and SpeI restriction enzyme sites at the upstream and downstream ends, respectively, was synthesised by Life Technologies. The sequence was released by digestion with BamHI and SpeI at 37° C. and gel purified. The DNA fragment was introduced into vector pRS426 (FIG. 9) cut with BamHI- and SpeI, to create plasmid pAU39, using T4 ligase (NEB) at room temperature for 2 hrs, and introduced into chemically-induced competent *E. coli* (DH5α) by heat shock for 0.5 minutes at 42° C. Plasmid pAU39 was subsequently isolated from the resulting ampicillin-resistant (100 µg/ml) colonies and the presence of the insert confirmed by restriction digest and subsequent sequencing.

SEQ ID NO 9:
BamHI
GGATCCTTTTCGTTCAATCAAGATATTTTATCACATTATTTCAAGGTTCA

ATGAATCATTCGAAGAATAGTAACGAATTCAGATATATTAAATAAAGGCA

CACATAATCTCTAAAGATTACAGTTTAATGGCTCTTTCAAAGTGTTTAGT

AATATATACACTAAATTTCTAAAATTCAGTAGTTATGGCGAAGTGGCCGA

GTGGTCTATGGCGCTAGCTTCAGGTGAAAGCAATTGCTAGTCTACGTATG

TGGGCGTGGGTTCGAACCCCACCTTCGTCAATATAATTTTTTATATCATG

TTAATGGAATTGAGAAAAACTAGT
SpeI

Effect of Fission Yeast tRNA-LeuCAG on Transgene Expression in Budding Yeast

Figure 10:
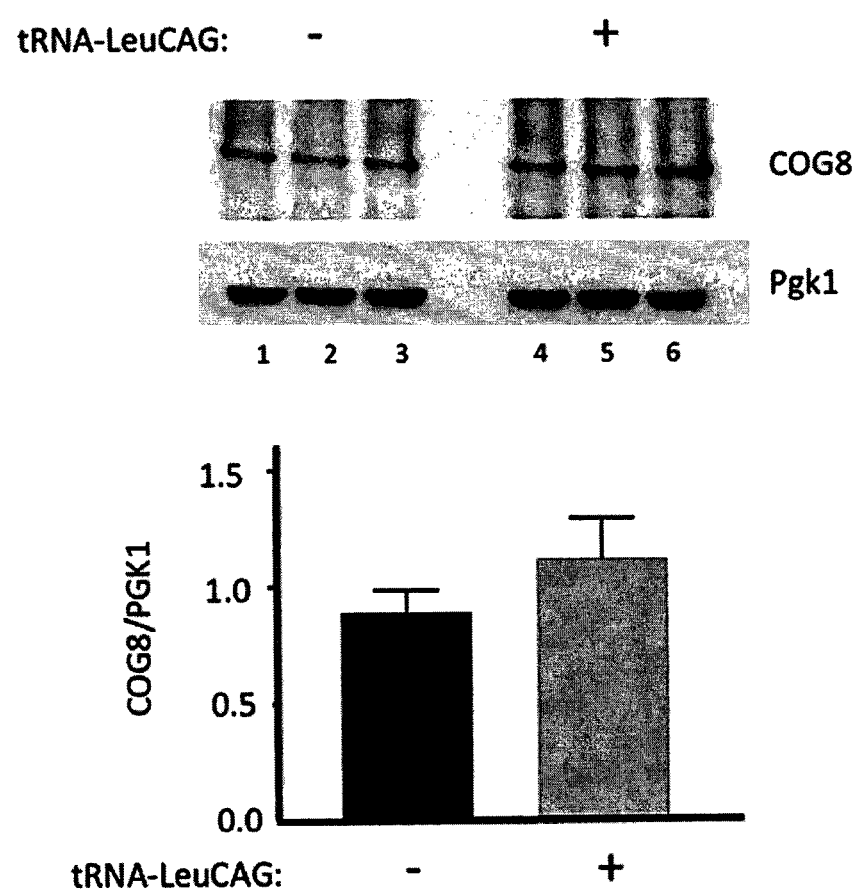
FIG. 10: Illustrates expression of COG8 and Pgk1, as determined by western blot, in *S. cerevisiae* with or without plasmid pAU39 expressing tRNA-LeuCAG (n=3)

*Saccharomyces cerevisiae* strain COG8-TAP (genotype his3Δ1 leu2Δ0 met15Δ0 ura3Δ0, COG8-TAP::HIS3, Mat a) was transformed using lithium acetate with pAU39 or empty pRS426 vector. Transformants were grown in standard minimal media (SD, lacking amino acids where appropriate for plasmid selection). 5 OD$_{600}$ unit equivalents of cells were harvested from liquid cultures in log phase and resuspended in 120 µl lysis buffer prior to incubation at 95° C. for 2 min and vortexing for 3 min in the presence of 100 µg glass beads (425-600 µm, acid washed). Lysates were resolved by 8% SDS PAGE and then analysed by western blotting with antibodies against COG8 and loading control Pgk1, as above (FIG. 10).

Figure 11:
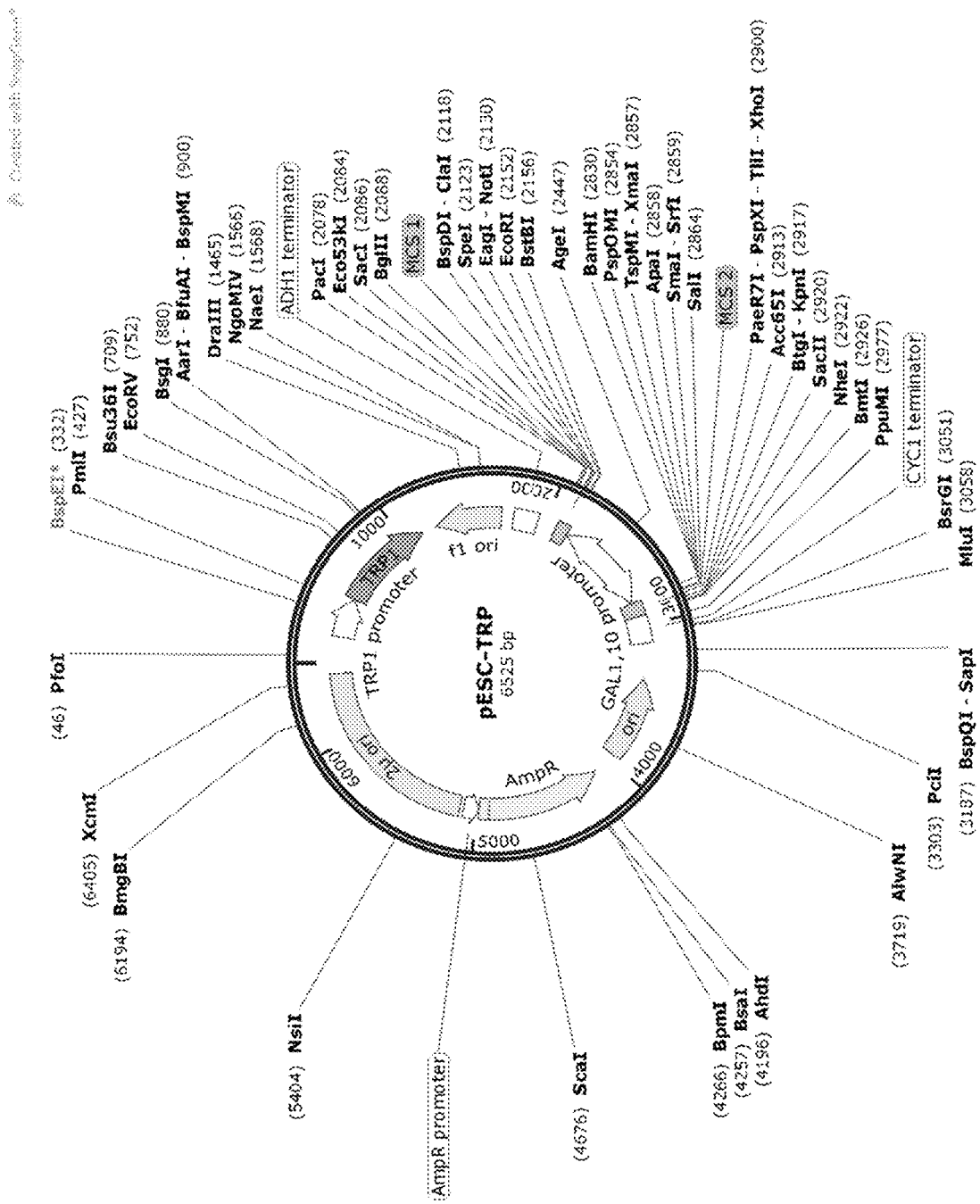
FIG. 11: Illustrates vector pESC-TRP, which was used to express in *S. cerevisiae* the turmeric enzyme diketide-CoA synthase (DCS)
Figure 12:
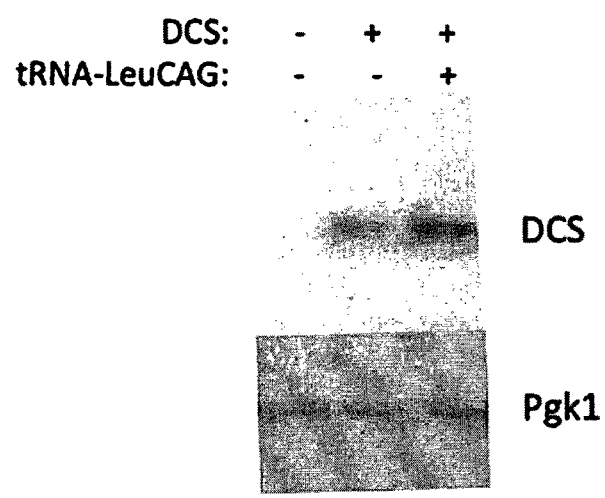
FIG. 12: Illustrates expression of DCS and Pgk1, as determined by western blot, in *S. cerevisiae* with or without plasmid pAU39 expressing tRNA-LeuCAG.

Strain G175 (ADE2 MET his3 leu2 ura3 trp1 TAG+SE+, Mat α) was also transformed with pAU39 or empty pRS426, along with vector pESC-TRP (FIG. 11) with or without a transgene containing the coding sequence of diketide-CoA synthase (DCS; AB495006.1), taken from turmeric (*Curcuma longa*), attached to a Myc tag. This sequence contains 17 CTG codons that depend on wobble for expression in native *S. cerevisiae*, but not after introduction of the exogenous tRNA-LeuCAG gene on pAU39. Expression of DCS was measured by western blotting, as above, with antibody against the Myc tag (FIG. 12).

Example 1

Figure 2:
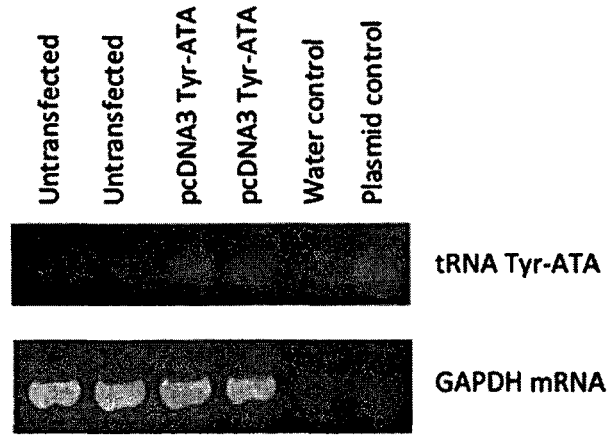
FIG. 2: Illustrates RT-PCR assay demonstrating expression of human tRNA Tyr-ATA gene in stably-transfected CHO cells.
Figure 4:
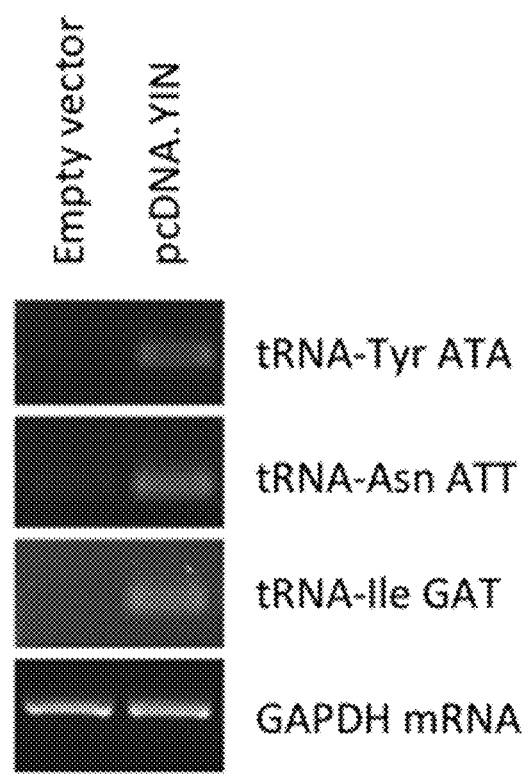
FIG. 4: Illustrates RT-PCR assay demonstrating expression of human tRNA Tyr-ATA, tRNA Asn-ATT and tRNA Ile-GAT genes in CHO cells transfected with pcDNA.YIN.
Figure 5:
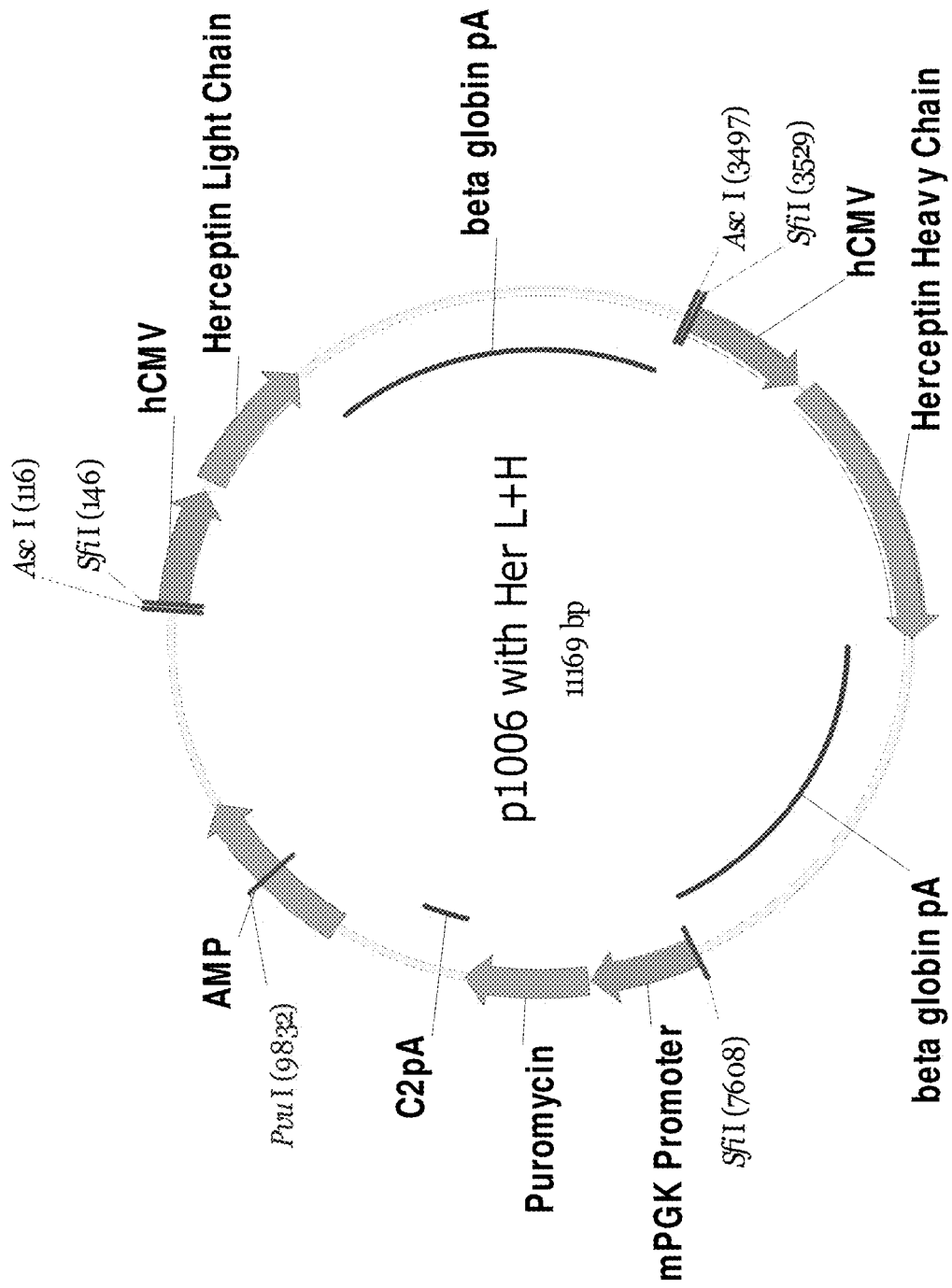
FIG. 5: Illustrates the expression vector pCET1006L&H encoding Herceptin light and heavy chains.
Figure 7:
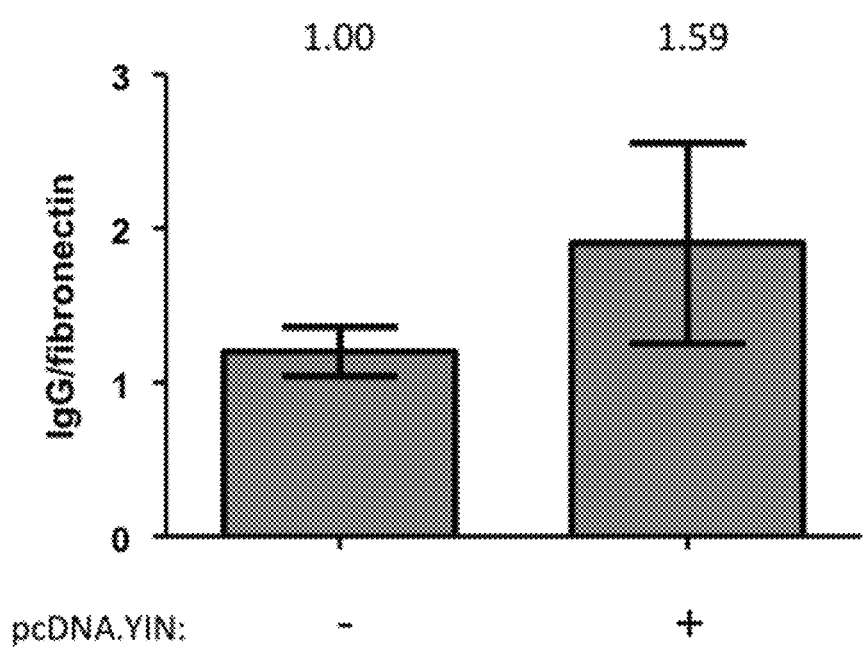
FIG. 7: Illustrates the relative expression of secreted Herceptin (trastuzumab) by matched clones of cells stably transfected with pCET1006L&H with or without pcDNA.YIN. The ratio of secreted Herceptin (trastuzumab) relative to secreted fibronectin (a CHO gene product, control) was increased by ~59% with pcDNA.YIN (n=4)

CHO cells do not have genes for tRNA-IleGAT, tRNA-AsnATT or tRNA-TyrATA and therefore rely on wobble to decode TAT, AAT and ATC codons. To allow wobble-independent decoding of these codons, we made and introduced a construct, pcDNA.YIN, carrying human tRNA-IleGAT, tRNA-AsnATT and tRNA-TyrATA genes. A DNA fragment containing the tRNA14-TyrATA gene from human chromosome 2 was synthesized and cloned (FIG. 1). The construct was stably transfected into CHO cells and RT-PCR analysis confirmed expression of the transgene (FIG. 2). The same approach was used to introduce a synthetic assembly (FIG. 3), in pcDNA.YIN, expressing human tRNA-TyrATA, tRNA-AsnATT and tRNA-IleGAT. Expression of all three human tRNAs in recipient CHO cells was confirmed by RT-PCR (FIG. 4). The effect of these tRNAs was tested on expression of Herceptin (trastuzumab) in CHO cells stably transfected with pCET1006L+H expression vector (FIG. 5). These cells were transfected with empty vector, pcDNA.YIN and/or pSUPER-7SL and secreted Herceptin (trastuzumab) was harvested and quantified (FIG. 6). Transient transfection of pcDNA.YIN was found to raise Herceptin expression by ~20%. This enhancement was boosted to ~49% by cotransfection of pSUPER-7SL, a construct containing the human RN7SL1 gene, that encodes 7SL RNA. In stable transfectants, genomic incorporation of pcDNA.YIN was found to raise by ~59% expression of Herceptin (trastuzumab), relative to the parental clone without pcDNA.YIN (FIG. 7). Mass spectrometry was used to ascertain rates of lysine misincorporation in the secreted antibody due to misreading of the wobble-dependent AAT codon for asparagine. Such errors were detected at 4 positions, with frequencies up to ~0.28%. These errors were suppressed by 4- to 32-fold in matched cells carrying the pcDNA.YIN, where the exogenous tRNAAsn-ATT allows direct decoding of the AAT codon without wobble (FIG. 8). Overall, these experiments with a therapeutic antibody demonstrate increased production and decreased misincorporation following introduction into CHO cells of exogenous tRNAs that reduce dependence on wobble.

Example 2

*S. cerevisiae* relies on wobble to decode the CTG codon for leucine, as it has no tRNA-LeuCAG. To remove the wobble-dependence of this codon, we created a strain of *S. cerevisiae* that carries an exogenous tRNA-LeuCAG gene from *Schizosaccharomyces pombe*. The effect of this tRNA was measured on expression of genes that are rich in CTG codons. A DNA fragment containing the trna49-LeuCAG gene from chromosome 1 of *S. pombe* was synthesized and cloned into pRS426 (FIG. 9) to create plasmid pAU39. Western blotting was used to determine the effect of pAU39 on expression in *S. cerevisiae* of COG8 (FIG. 10) and DCS (FIG. 12). There are 10 CTG codons in COG8 and 17 in DCS, but none in Pgk1, an endogenous protein that was used as control. For both COG8 and DCS, expression was enhanced by the tRNA-LeuCAG gene on pAU39 relative to the empty vector control. We conclude that the efficacy of *S. cerevisiae* as a platform for expressing transgenes can be improved by introduction of exogenous tRNA to reduce dependence on wobble.

The invention claimed is:

1. An isolated eukaryotic cell modified by transfection or transformation with:
   (i) a first expression vector adapted for eukaryotic expression comprising a transcription cassette, the transcription cassette comprising at least one nucleotide sequence encoding a transfer RNA (tRNA) molecule, the tRNA molecule including an anticodon nucleotide sequence selected from the group consisting of AGC, GGC, CGC, UGC, ACC, GCC, CCC, UCC, AGG, GGG, CGG, UGG, AGU, GGU, CGU, UGU, AAC, GAC, CAC, UAC, AAA, GAA, AUU, GUU, CUU, UUU, AUC, GUC, CUC, UUC, AGA, GGA, CGA, UGA, ACU, GCU, ACG, GCG, CCG, UCG, CCU, UCU, AAG, GAG, CAG, UAG, CAA, UAA, AAU, GAU, UAU, CAU, AUA, GUA, ACA, GCA, AUG, GUG, CUG, UUG, or CCA,
   wherein said tRNA molecule comprising said anticodon nucleotide sequence is absent from said eukaryotic cell prior to transfection or transformation with said first expression vector; and
   (ii) a second expression vector encoding a recombinant protein,
   wherein said tRNA molecule comprising said anticodon sequence corrects base mismatches at the third nucleotide position in a messenger RNA (mRNA) codon encoding said recombinant protein to improve translation efficiency and/or decrease amino acid mis-incorporation as a consequence of degeneracy in the genetic code; and
   wherein correction of said base mismatches reduces reliance of the eukaryotic cell on wobble during translation of said mRNA.

2. The isolated eukaryotic cell according to claim 1, wherein said first expression vector and said second expression vector are adapted for expression in a mammalian cell, fungal cell, insect cell, or plant cell.

3. The isolated eukaryotic cell according to claim 1, wherein said isolated eukaryotic cell is an insect, plant, fungal or mammalian cell.

4. The isolated eukaryotic cell according to claim 3 wherein said isolated mammalian cell is a non-human mammalian cell.

5. The isolated eukaryotic cell according to claim 3, wherein said isolated mammalian cell is a Chinese Hamster Ovary, (CHO), HEK293, NS0 or CAP cell.

6. The isolated eukaryotic cell according to claim 3 wherein said fungal cell is *Saccharomyces cerevisae*, *Schizosaccharomyces pombe*, *Yarrowia lipolytica*, *Pichia pastoris*, *Aspergillus* spp., *Kluyveromyces lactis* or *Trichoderma reesei*.

7. The isolated eukaryotic cell according to claim 1, wherein said transcription cassette comprises nucleotide sequences encoding 1, 2, 3, 4, 5, 6, 7, 8, 9, 10, 11, 12, 13, 14 or 15 different tRNAs.

8. The isolated eukaryotic cell according to claim 1, wherein said at least one nucleotide sequence encoding a tRNA molecule encodes Ala-tRNA, Arg-tRNA, Asp-tRNA, Asn-tRNA, Cys-tRNA, Glu-tRNA, Gln-tRNA, Gly-tRNA, His-tRNA, Ile-tRNA, Leu-tRNA, Lys-tRNA, Met-tRNA, Phe-tRNA, Pro-tRNA, Ser-tRNA, Thr-tRNA, Trp-tRNA, Tyr-tRNA or Val-tRNA.

9. The isolated eukaryotic cell according to claim 1, wherein said anticodon nucleotide sequence is cytosine and/or adenine rich.

10. The isolated eukaryotic cell according to claim 1, wherein said anticodon nucleotide sequence is uracil free.

11. The isolated eukaryotic cell according to claim 1, wherein said second expression vector encodes a therapeutic antibody.

12. The isolated eukaryotic cell according to claim 1, wherein said second expression vector encodes a pharmaceutical or therapeutic protein or peptide, or an industrial enzyme.

13. The isolated eukaryotic cell according to claim 1, wherein said isolated eukaryotic cell is further modified by transformation or transfection with a nucleic acid molecule comprising a 7SL nucleotide sequence.

14. The isolated eukaryotic cell according to claim 13, wherein said 7SL nucleotide sequence comprises the nucleotide sequence of SEQ ID NO: 10 or a nucleotide sequence comprising at least 90% nucleotide sequence identity to the nucleotide sequence of SEQ ID NO: 10.

15. An isolated mammalian cell modified by transfection or transformation with
   (i) a first expression vector adapted for mammalian expression comprising a transcription cassette, the transcription cassette comprising at least one nucleotide sequence encoding a transfer RNA (tRNA) molecule(s), the tRNA molecule(s) including an anticodon nucleotide sequence selected from the group consisting of AGC, GGC, CGC, UGC, ACC, GCC, CCC, UCC, AGG, GGG, CGG, UGG, AGU, GGU, CGU, UGU, AAC, GAC, CAC, UAC, AAA, GAA, AUU, GUU, CUU, UUU, AUC, GUC, CUC, UUC, AGA, GGA, CGA, UGA, ACU, GCU, ACG, GCG, CCG, UCG, CCU, UCU, AAG, GAG, CAG, UAG, CAA, UAA, AAU, GAU, UAU, CAU, AUA, GUA, ACA, GCA, AUG, GUG, CUG, UUG, or CCA, wherein said tRNA molecule(s) comprising said anticodon nucleotide sequence is absent from said mammalian cell prior to transfection or transformation with said first expression vector; and (ii) a second expression vector encoding a recombinant antibody, wherein said tRNA molecule(s) comprising said anticodon sequence corrects base mismatches at the third nucleotide position in a messenger RNA (mRNA) codon encoding said recombinant antibody to improve translation efficiency and/or decrease amino acid misincorporation as a consequence of degeneracy in the genetic code, and wherein correction of said base mismatches reduces reliance of the mammalian cell on wobble during translation of said mRNA.

* * * * *